US009585994B2

(12) United States Patent
Cho

(10) Patent No.: US 9,585,994 B2
(45) Date of Patent: Mar. 7, 2017

(54) BLOOD PURIFYING FILTER AND BLOOD PURIFYING APPARATUS HAVING THE SAME

(71) Applicant: Taebeom Cho, Daejeon (KR)

(72) Inventor: Taebeom Cho, Daejeon (KR)

(73) Assignee: HUMAN BIOMED, INC.VT (US)

( * ) Notice: Subject to any disclaimer, the term of this patent is extended or adjusted under 35 U.S.C. 154(b) by 297 days.

(21) Appl. No.: 14/243,137

(22) Filed: Apr. 2, 2014

(65) Prior Publication Data

US 2015/0283315 A1    Oct. 8, 2015

(51) Int. Cl.
| | |
|---|---|
| *A61M 1/34* | (2006.01) |
| *B01D 61/24* | (2006.01) |
| *B01D 61/58* | (2006.01) |
| *B01D 63/04* | (2006.01) |
| *A61M 1/16* | (2006.01) |
| *B01J 20/28* | (2006.01) |
| *A61M 1/36* | (2006.01) |

(52) U.S. Cl.
CPC ............ *A61M 1/3417* (2014.02); *A61M 1/16* (2013.01); *A61M 1/3472* (2013.01); *A61M 1/3479* (2014.02); *A61M 1/3486* (2014.02); *A61M 1/3496* (2013.01); *A61M 1/3679* (2013.01); *B01D 61/58* (2013.01); *B01D 63/04* (2013.01); *B01D 63/043* (2013.01); *B01J 20/2805* (2013.01); *A61M 2205/75* (2013.01); *B01D 2311/2626* (2013.01); *B01D 2311/2649* (2013.01); *B01D 2313/21* (2013.01); *B01D 2319/02* (2013.01)

(58) Field of Classification Search
CPC .............. A61M 1/3472; A61M 1/3486; A61M 1/3679; A61M 1/3496; A61M 1/3417; A61M 1/3479; A61M 2205/75; A61M 1/16; B01D 61/243; B01D 61/58; B01D 2311/2626; B01D 2313/08; B01D 2313/21; B01D 2313/40; B01D 2319/02; B01D 63/04; B01D 63/043; B01D 2311/2649; B01J 20/2805
See application file for complete search history.

(56) References Cited

U.S. PATENT DOCUMENTS

| | | | |
|---|---|---|---|
| 7,285,106 B2 * | 10/2007 | Collins ................ | B01D 61/142 210/321.64 |
| 7,311,832 B2 * | 12/2007 | Demmer ............ | B01J 20/28004 210/500.22 |

(Continued)

FOREIGN PATENT DOCUMENTS

KR    10-2006-0057176    5/2006

*Primary Examiner* — John Kim
(74) *Attorney, Agent, or Firm* — Lee Global Patent, LLC

(57) ABSTRACT

Provided are a blood purifying filter and a blood purifying apparatus including the same. The blood purifying filter includes a plasma separation filter, a hemodialysis filter, a housing, and a plasma outlet. The plasma separation filter separates plasma from blood. The hemodialysis filter removes toxins and waste products from blood. The housing provides installation spaces for the plasma separation filter and the hemodialysis filter and defines a plasma flow section outside the plasma separation filter and the hemodialysis filter. The plasma outlet is provided at one side of the housing to allow plasma passing the plasma flow section to be discharged out of the blood purifying filter.

14 Claims, 16 Drawing Sheets

(56) References Cited

U.S. PATENT DOCUMENTS

| | | | |
|---|---|---|---|
| 7,775,375 B2 * | 8/2010 | Palumbo | B01D 63/024 210/252 |
| 2003/0010205 A1 * | 1/2003 | Bikson | B01D 46/003 95/52 |
| 2010/0282662 A1 * | 11/2010 | Lee | A61M 1/3472 210/266 |
| 2013/0220913 A1 * | 8/2013 | Cohen | B01D 24/002 210/275 |

* cited by examiner

BLOOD PURIFYING FILTER AND BLOOD PURIFYING APPARATUS HAVING THE SAME

BACKGROUND OF THE INVENTION

The present invention relates to a blood purifying filter and a blood purifying apparatus including the blood purifying filter, which are configured to separate plasma from blood of a patient using a plasma separation filter, remove hepatic toxins from the separated plasma using adsorbents, such as activated charcoal or anion exchange resin, and simultaneously perform hemodialysis which removes water-soluble toxins and uremic toxins from blood.

Liver performs many functions such as a metabolic function of treating various nutrients existing in our body, a function to store nutrients required by our body, a synthesizing function to synthesize gall juice and albumin, and a function to detoxify various toxins brought into our body such as alcohol or drug. Accordingly, when a liver is damaged, the substances such as ammonia and bilirubin to be removed from a body by the hepatic metabolism are accumulated in the body. The accumulation causes complications such as jaundice, hepatic encephalopathy, and multiple organ failure.

Liver is known to have a certain extent of self-recovery even when its functioning is degraded due to illnesses. In case of acute liver failure, however, since the patient cannot live by the time the live recovers by itself, a liver transplant is regarded as the only cure. As shown by the liver transplant data published by OPTN/SRTR Annual Report in 2010, only 30% to 40% of the patients waiting for a liver transplant actually get the treatment. An artificial liver treatment is required for liver failure patients to serve the function until a liver transplant or self-recovery.

Artificial liver apparatuses currently in clinical use are limited only to MARS of Gambro Inc. and Prometheus of FMC. MARS removes hepatic toxins from blood by adding a plasma protein called albumin in dialysis fluid. Since albumin is expensive, MARS comes to a costly treatment. Prometheus has such configuration that plasma is separated from blood to be filtered through ion resin adsorbent for removal of toxins existing in the plasma and then hemodialysis is performed after the plasma separation and adsorption. Accordingly, Prometheus apparatus has a complicated system including a plasma separation filter, two adsorption filters removing toxins from plasma, and hemodialysis process, giving rise to a high treatment cost like MARS.

In order to solve such limitations of typical artificial liver systems, Korean Patent No. 1071402 entitled "Apparatus for Purifying Blood" discloses an apparatus that is configured to remove toxins from plasma without using expensive albumin and integrate plasma separation and absorption processes into a single filter. By implementing plasma separation and adsorption processes in a single filter, the entire artificial liver system is simplified from the typical artificial liver apparatuses. However, the system still requires additional hemofiltration or hemodialysis process. That is, in a case of a patient who needs intensive blood purifying treatment for liver failure, the removal of water-soluble toxins by hemodialysis or hemofiltration is as important as the removal of liver toxins or protein-bound toxins through adsorption.

As described above, since typical artificial liver apparatuses require hemodialysis filter, plasma separation filter, and a plurality of other adsorption filers, they are costly. Since the filters are all separately arranged to allow blood or plasma to flow against gravity, each filter needs room for its arrangement. Accordingly, there is a limitation in that the system is big in size and its setting and preparation for treatment take much time.

SUMMARY OF THE INVENTION

The present invention provides a blood purifying filter and an apparatus having the blood purifying filter, which efficiently purifies blood of a patient, enables simplification and miniaturization of the whole blood purifying apparatus, and provides convenience in installation and use, by integrating a plasma separation process for separating plasma from blood, an adsorption process for removing toxins from the separated plasma, and a hemodialysis process for removing uremic toxins from blood by a single filter.

Embodiments of the present invention provide blood purifying filters including: a plasma separation filter separating plasma from blood; a hemodialysis filter removing toxins and waste products from blood; a housing providing installation spaces for the plasma separation filter and the hemodialysis filter and defining a plasma flow section outside the plasma separation filter and the hemodialysis filter; and a plasma outlet provided at one side of the housing to allow plasma passing the plasma flow section to be discharged out of the blood purifying filter.

The housing may include a wall having a cylindrical shape, a lower cap coupled to the plasma separation filter at a lower side of the wall, and an upper cap coupled to the hemodialysis filter at an upper side of the wall. The lower cap and the upper cap may have a blood port for the flow of blood and an insertion groove so as to be easily coupled to each filter. The upper cap may additionally have a dialysate flow port for the flow of dialysate, and a connector may be provided to connect the plasma separation filter and the hemodialysis filter without a leakage of blood.

The plasma separation filter and the hemodialysis filter include a housing defining an internal space thereof and a separation membrane accommodated in the internal space of the housing. The internal space of the housing may be divided into a blood flow region and a plasma or dialysate flow region by the separation membrane. The plasma separation filter housing may have plasma flow holes such that separated plasma can flow into the plasma flow section, and the hemodialysis filter housing may have dialysate flow holes for the flow of dialysate.

Due to the coupling of the upper cap and the hemodialysis filter, the dialysate flow port provided in the upper cap and the dialysate flow hole provided in the hemodialysis filter housing may be connected to each other to form a dialysate flow passage, allowing dialysate to be supplied or discharged through the dialysate flow passage. Thus, when the blood purifying filter has one dialysate flow passage, the supply of dialysate to the hemodialysis filter and the discharge of dialysate out of the hemodialysis filter may alternately occur.

An adsorbent may be provided in the plasma flow section to remove toxins and waste products from plasma. The number and type of the adsorbent included in the blood purifying filter may be modified according to the purpose of the blood purifying treatment. The plasma flow hole may be provided closely to the lower cap of the plasma separation filter housing, and the plasma outlet may be provided closely to the upper cap or on the wall at a side of the upper cap, such that plasma can sufficiently contact the adsorbent inside the plasma flow section and then be discharged. Finally, any adsorbent must not move through the plasma flow hole and the plasma outlet. When two or more kinds of adsorbent are used, a separation wall may be disposed to prevent the two or more kinds of adsorbent from mixing with each other.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Hereinafter, a blood purifying filter according to a first embodiment of the present invention will be described in detail with reference to the accompanying drawings.

Figure 1:
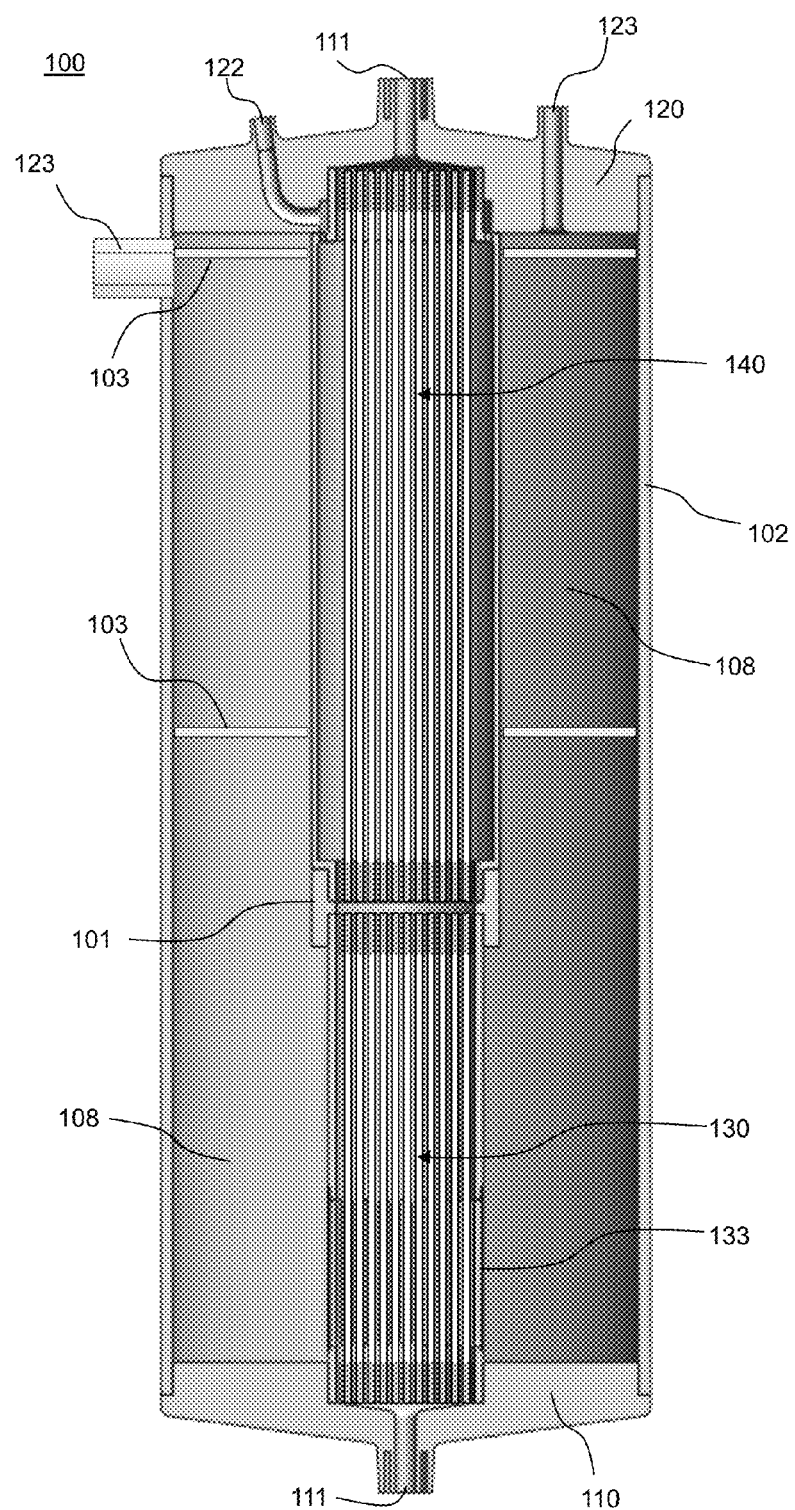
FIG. 1 is a cross-sectional view illustrating an internal configuration of a blood purifying filter according to a first embodiment of the present invention.
Figure 2:
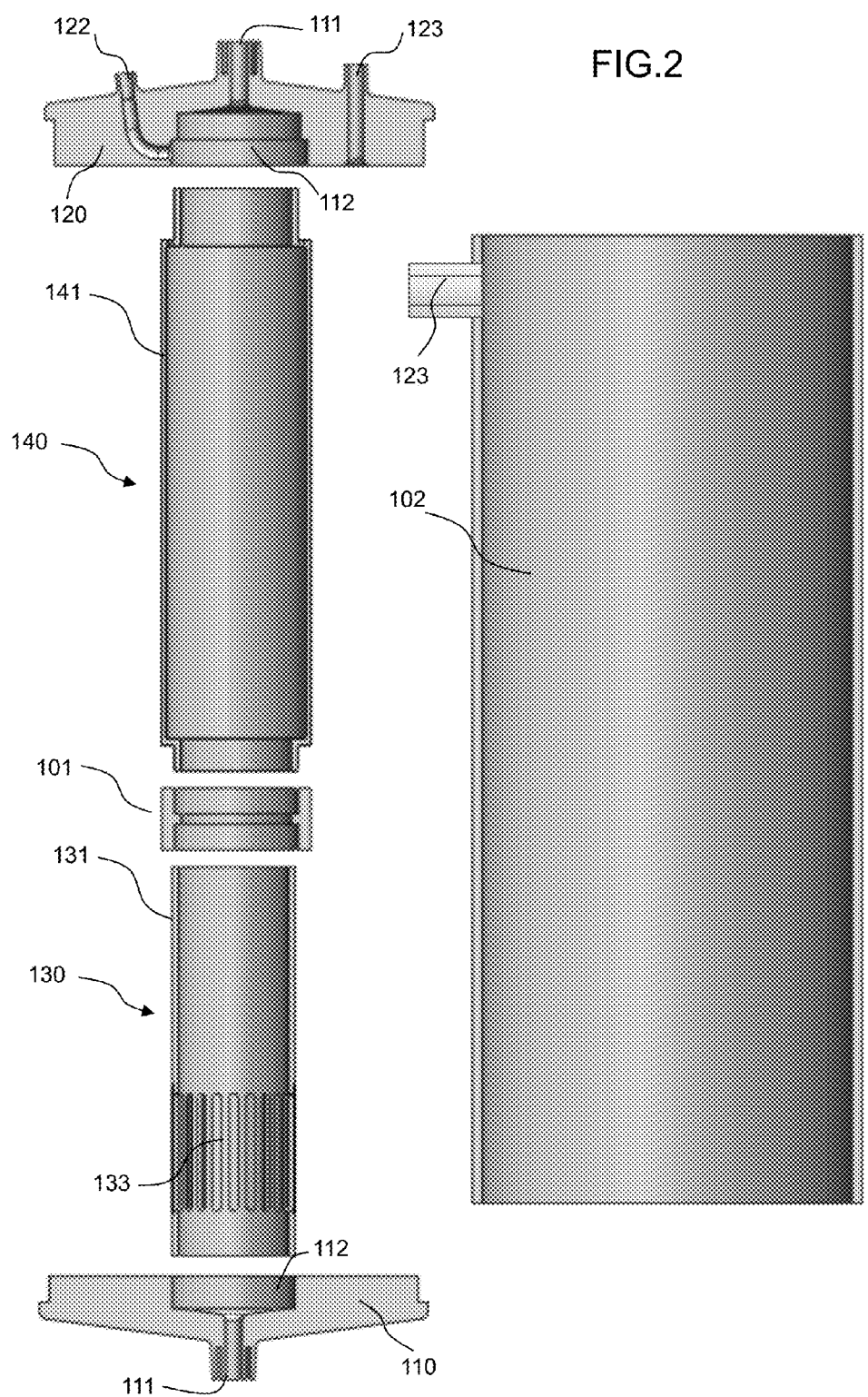
FIG. 2 is an exploded cross-sectional view illustrating a blood purifying filter according to a first embodiment of the present invention, which shows a combination structure of a plasma separation filter, a hemodialysis filter, and a housing including a lower cap and an upper cap.
Figure 3:
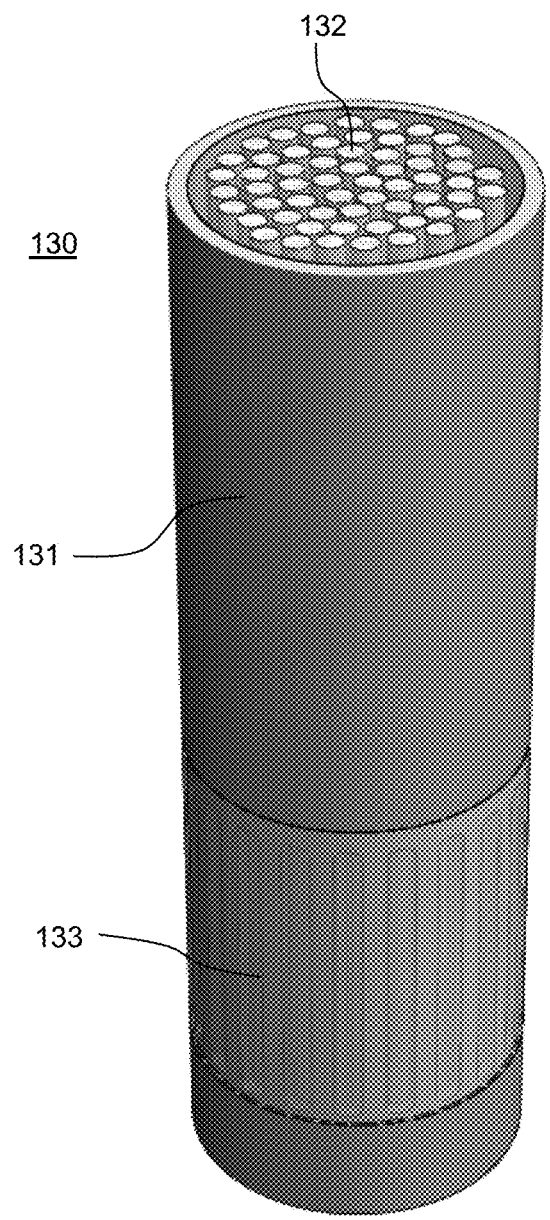
FIG. 3 is a perspective view of a plasma separation filter.
Figure 4:
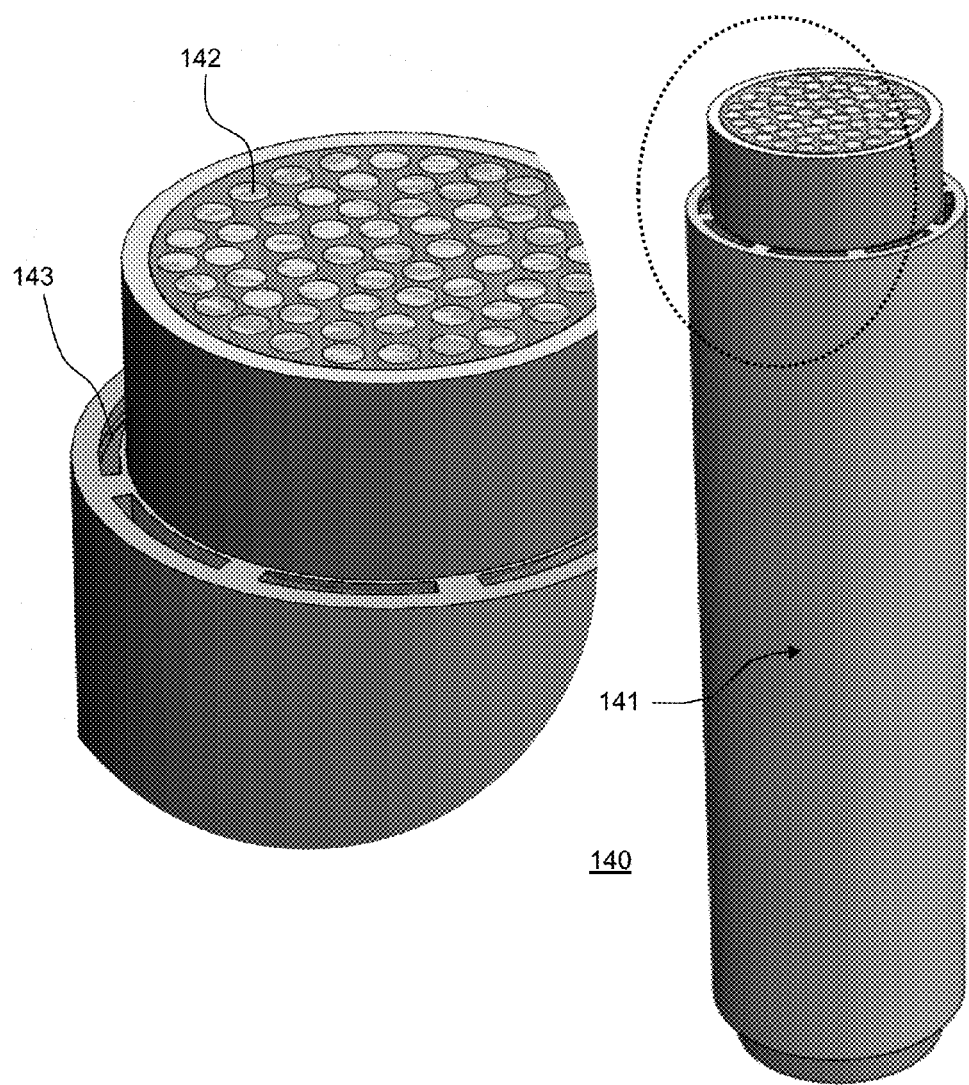
FIG. 4 is a perspective view of a hemodialysis filter.
Figure 5:
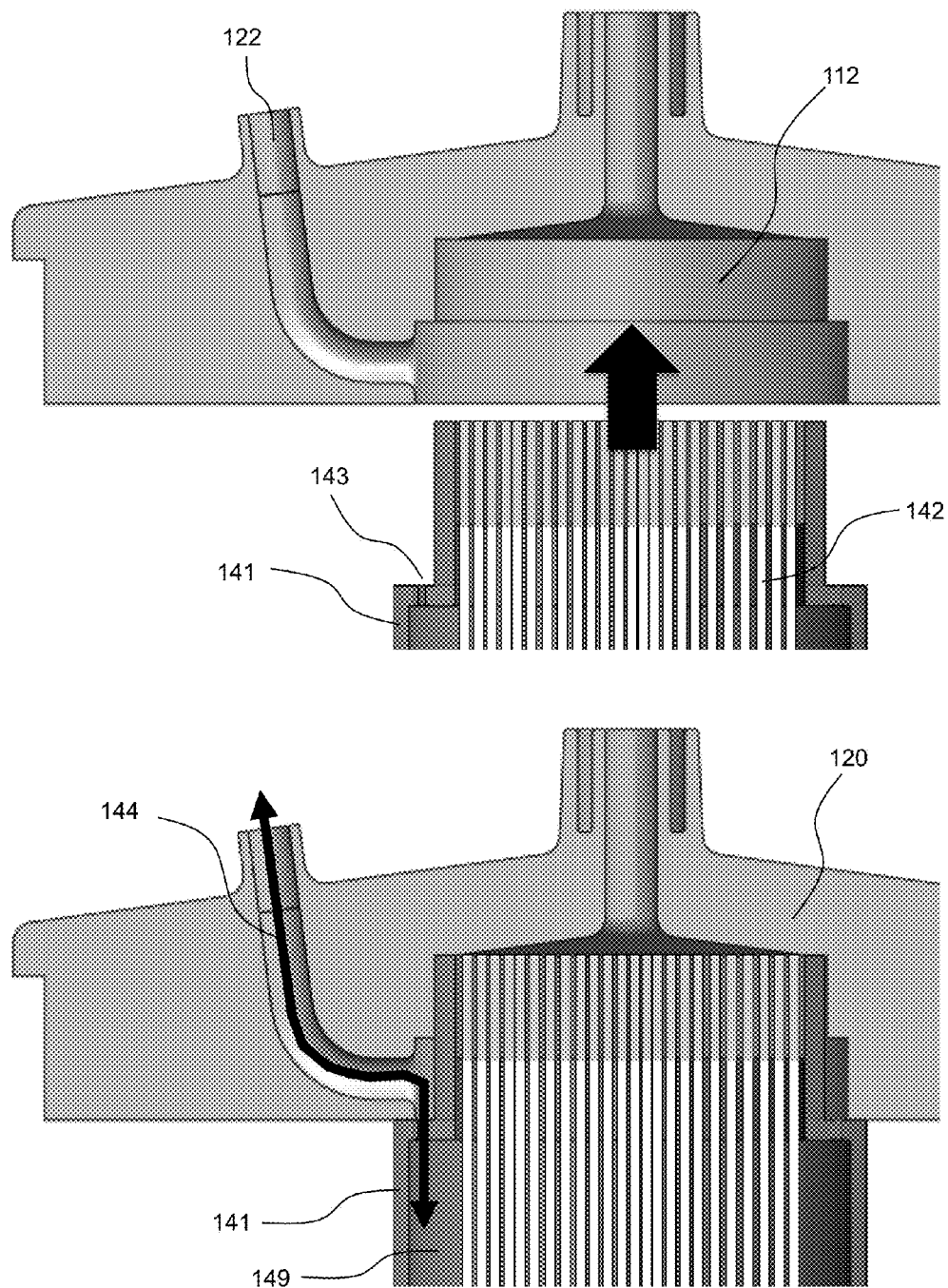
FIG. 5 is a magnified cross-sectional view illustrating a combination structure of a hemodialysis filter and an upper cap.

FIG. 1 is a cross-sectional view illustrating an internal configuration of a blood purifying filter 100 according to a first embodiment of the present invention, and FIG. 2 is an exploded cross-sectional view of the blood purifying filter 100. FIGS. 3 and 4 are perspective views illustrating a plasma separation filter 130 and a hemodialysis filter 140, respectively, and FIG. 5 is a cross-sectional view illustrating a combination of the hemodialysis filter and an upper cap 120.

As shown in FIG. 1, the blood purifying filter 100 may include a plasma separation filter 130, a hemodialysis filter 140, a housing, and a plasma outlet 123. The plasma separation filter 130 separates plasma from blood that is introduced from one side of the blood purifying filter 100. The hemodialysis filter 140 which may be connected to the plasma separation filter 130 removes toxins and waste products from blood. The housing provides installation spaces for the plasma separation filter 130 and the hemodialysis filter 140, and defines a plasma flow section 108 outside the plasma separation filter 130 and the hemodialysis filter 140. The plasma outlet 123 may be provided at ones side of the housing to allow plasma passing the plasma flow section 108 to be discharged out of the blood purifying filter 100.

The housing includes a wall 102 having a cylindrical shape, a lower cap 110 coupled to the plasma separation filter 130 at a lower side of the wall 102, and an upper cap 120 coupled to the hemodialysis filter 140 at an upper side of the wall 102. As shown in FIG. 2, the lower cap 110 and the upper cap 120 may be provided with blood ports 111 for the flow of blood and insertion grooves 112 so as to be easily coupled to the plasma separation filter 130 and the hemodialysis filter 140, respectively. The upper cap 120 may be additionally provided with a dialysate flow port 122 for the flow of dialysate. Also, the blood purifying filter 100 may include a connector 101 that connects between the plasma separation filter 130 and the hemodialysis filter 140 to prevent a leakage of blood. The connector 101 may vary in dimension and shape to strengthen the coupling of the hemodialysis filter 140 and the plasma separation filter 130.

As shown in FIG. 3, the plasma separation filter 130 includes a plasma separation filter housing 131 defining an internal space thereof and a plasma separation membrane 132 disposed in the internal space of the plasma separation filter housing 131. The internal space of the plasma separation filter housing 131 is divided into a blood flow region and a plasma flow region by the plasma separation membrane 132. One end of the plasma separation filter 130 may be connected to the hemodialysis filter 140 through the connector 101, and the other end of the plasma separation filter 130 may be coupled to the lower cap 110, allowing blood passing the blood port 111 in the lower cap 110 to flow into the blood flow region. Blood introduced from one side of the plasma separation filter 130 passes the blood flow region inside the plasma separation membrane 132 and is discharged to the other side of the plasma separation filter 130. In this case, plasma may be separated from blood by penetrating a side wall of the plasma separation membrane 132 in a radial direction. The plasma separation filter housing 131 may have plasma flow holes 133 such that separated plasma can flow into the plasma flow section 108. For smooth flow of plasma, the plasma flow holes 133 may be formed to surround the plasma separation filter housing 131 in a lateral direction.

As shown in FIG. 4, the hemodialysis filter 140 includes a hemodialysis filter housing 141 defining an internal space thereof and a hemodialysis membrane 142 disposed in the internal space of the hemodialysis filter housing 141. The internal space of the hemodialysis filter housing 141 is divided into a blood flow region and a dialysate flow region by the hemodialysis membrane 142. The hemodialysis filter housing 141 may have dialysate flow holes 143 for the flow of dialysate. As shown in FIG. 5, the hemodialysis filter 140 may be coupled to the upper cap 120, allowing the dialysate flow port 122 provided in the upper cap 120 and the dialysate flow holes 143 provided in the hemodialysis filter housing 141 to be connected to each other and thus forming a dialysate flow passage 144. Dialysate is supplied or discharged through the dialysate flow passage 144. Also, due to the coupling of the hemodialysis filter 140 and the upper cap 120, blood passing the blood port 111 provided in the upper cap 120 flows into the blood flow region inside the hemodialysis filter 140. That is, due to the coupling of the upper cap 120 and the hemodialysis filter 140, blood and dialysate are limited to flow into a predetermined region. Thus, blood and dialysate are prevented from flowing to other spaces except predetermined spaces by chemical adhesion of each coupling part of the upper cap 120 and the hemodialysis filter 140 or insertion of a soft O-ring such as silicone into each adhesion part.

Figure 6:
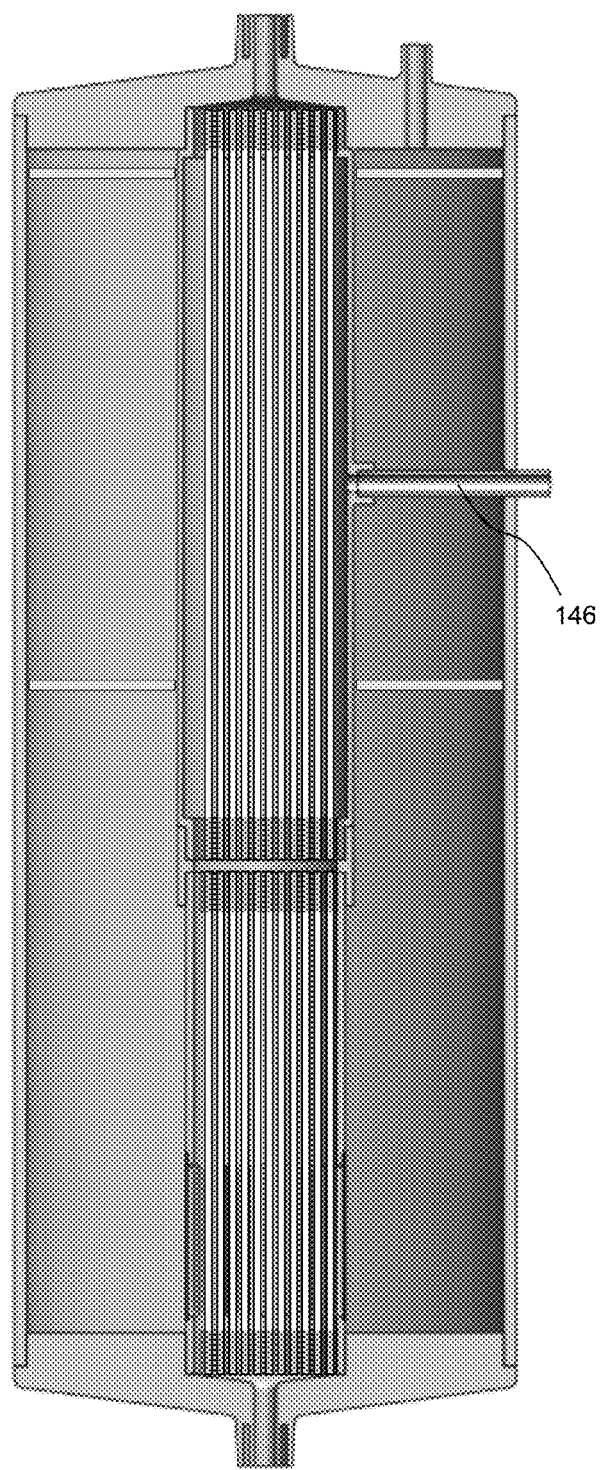
FIG. 6 is a cross-sectional view illustrating a blood purifying filter configured to have a dialysate passage penetrating a hemodialysis filter housing and a wall.
Figure 7:
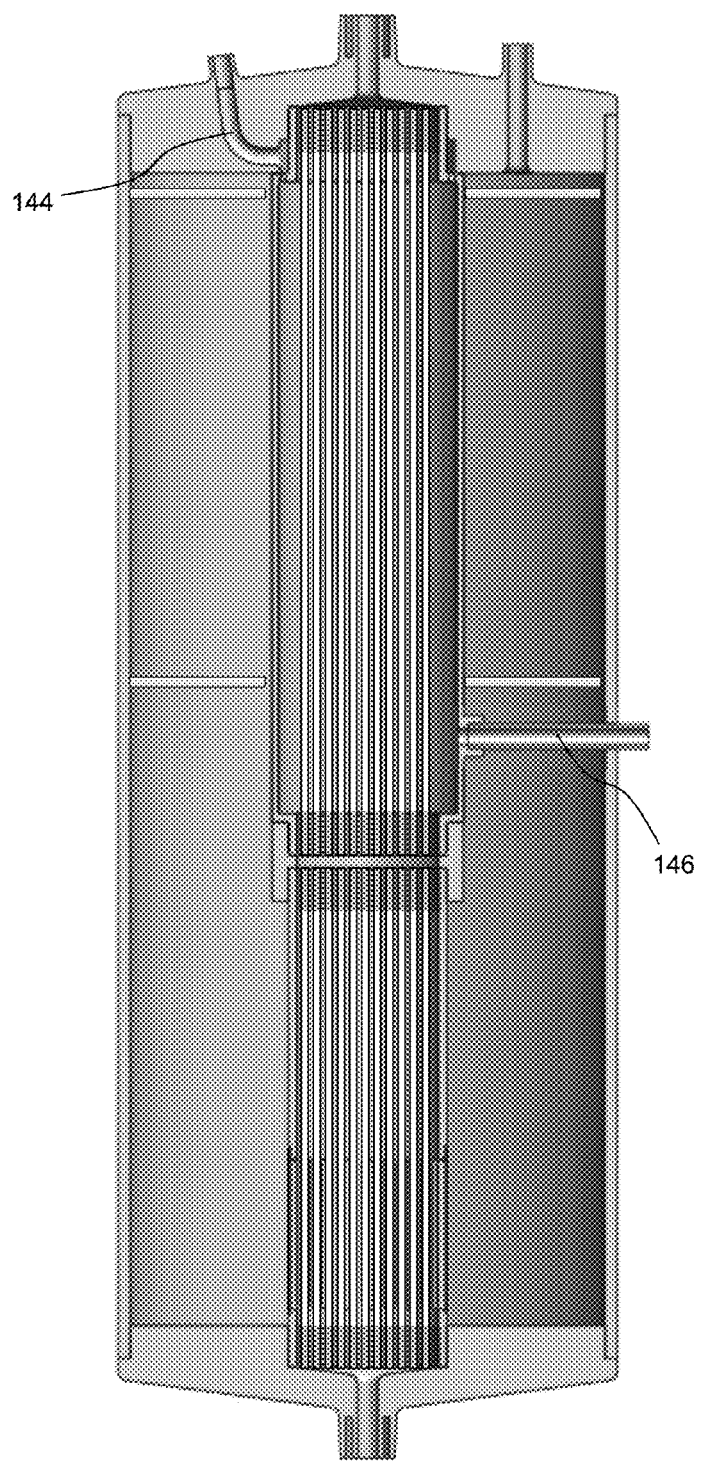
FIGS. 7 and 8 are cross-sectional views illustrating a blood purifying filter having two dialysate passages to divide inflow and outflow of dialysate.
Figure 8:
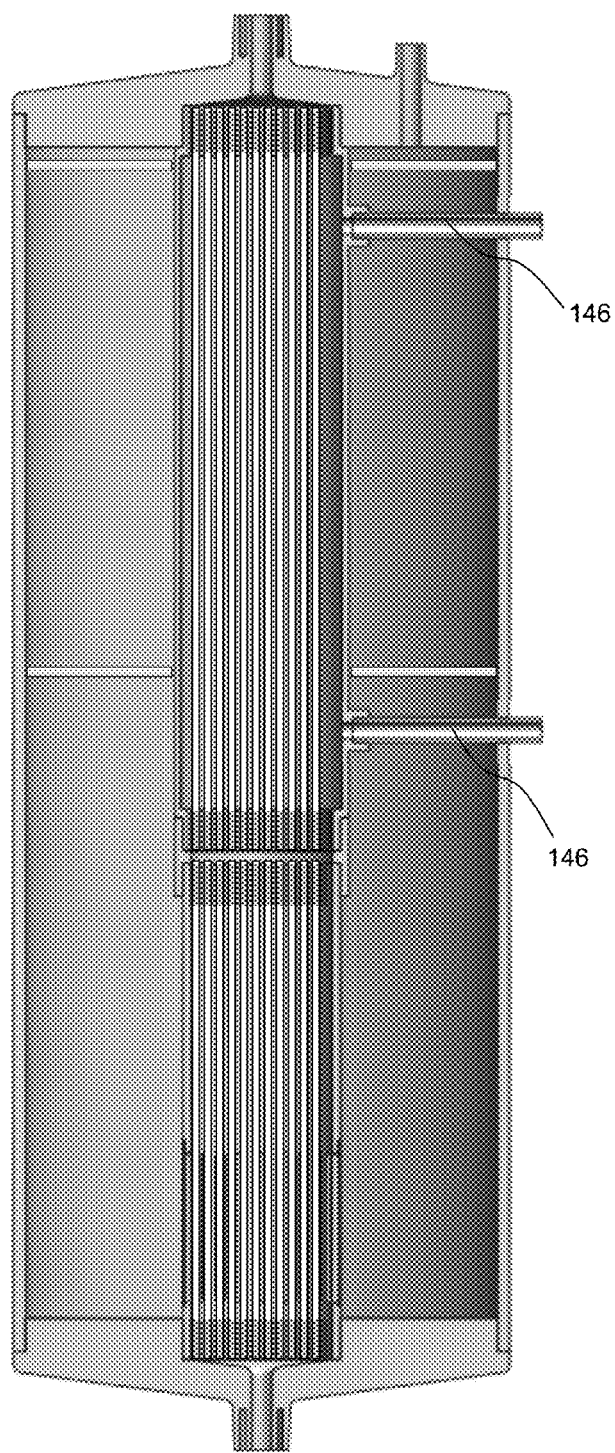
Figure 9:
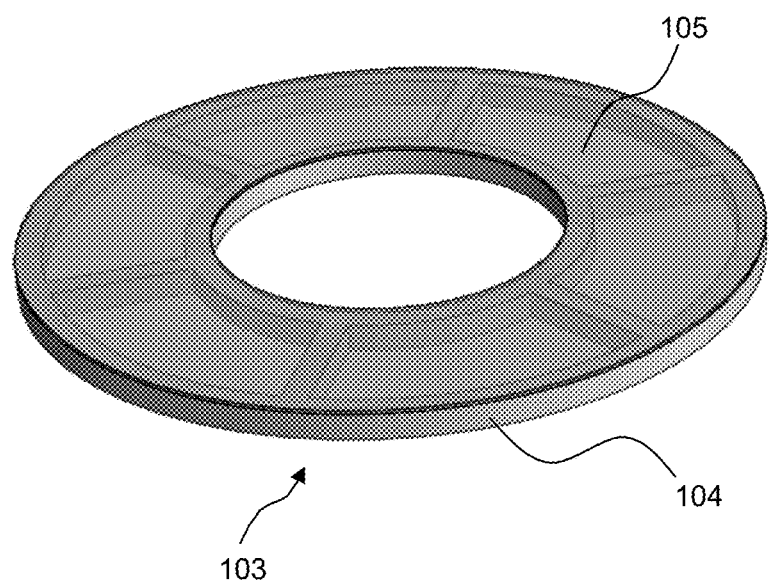
FIG. 9 is a perspective view of a separation wall.

The dialysate flow port 122, the dialysate flow hole 143, and the dialysate flow passage 144 configured by the connection thereof are not limited to the shape and location described in the drawings, and may be modified into other structures that can allow dialysate to flow. For example, as shown in FIG. 6, the dialysate flow port 122, the dialysate flow hole 143, and the dialysate flow passage 144 configured by the connection thereof may be modified into a wall flow passage 146 that is formed to penetrate the hemodialysis filter housing 141 and the wall 102. In addition, as shown in FIGS. 7 and 8, the dialysate flow passage 144 provided in the upper cap 120 and the wall flow passage 146 connecting the hemodialysis filter housing 141 and the wall 102 may be both provided in order to separate the inflow and outflow of dialysate, or two separated wall flow passages 146 may be provided to supply dialysate through one wall flow passage 146 and discharge dialysate through the other wall flow passage 146.

An adsorbent may be provided in the plasma flow section 108 to remove toxins and waste products from plasma. An anion exchange resin can remove electrically charged toxins such as bilirubin while being combined with plasma proteins by means of ion exchange mechanism. On the other hand, activated charcoal may be used to remove tryptophan and water-soluble toxin of a mesomolecule size by physical adsorption. The adsorbent may be used in a form of powder, particle, or block in which powder and particles are compressed. The adsorbent included in the blood purifying filter according to an embodiment of the present invention is not limited in the type and number, and may be modified according to the purpose of the blood purifying treatment.

Also, as shown in FIG. 1, the plasma flow holes 133 may be desirably provided closely to the lower cap 110 of the plasma separation filter housing 131 and the plasma outlets 123 may be provided in the upper cap 120 or on the wall 102 at a side of the upper cap 120, such that plasma can sufficiently contact the adsorbent inside the plasma flow section 108 and then be discharged.

The adsorbent must not move through the plasma flow hole 133 and the plasma outlet 123. For this, various methods may be used. For example, the plasma flow hole 133 or the plasma outlet 123 may be formed to have a size smaller than the adsorbent, or may be covered by a mesh filter with pores having a smaller size than the adsorbent. Also, the adsorbent may be covered by a mesh filter with pores having a smaller size than the adsorbent itself, or an adsorbent block in which powder or particles are compressed may be used. In addition, a separation wall 103 may be disposed between the adsorbent and the plasma flow hole 133 or between the adsorbent and the plasma outlet 123. The separation wall 103 may be manufactured to have pores of a smaller size than the adsorbent to inhibit the passing of adsorbent, or may be manufactured to have a structure in which a mesh filter 105 having pores of a smaller size than the adsorbent is attached to a support wall 104. Similarly, when two or more kinds of adsorbent are used, the adsorbents may be covered by a mesh filter with pores of a smaller size than the adsorbents in order to prevent the adsorbents from mixing. Also, an adsorbent block in which powder or particles are compressed may be used, or a separation wall 103 may be disposed between the adsorbents.

Figure 10:
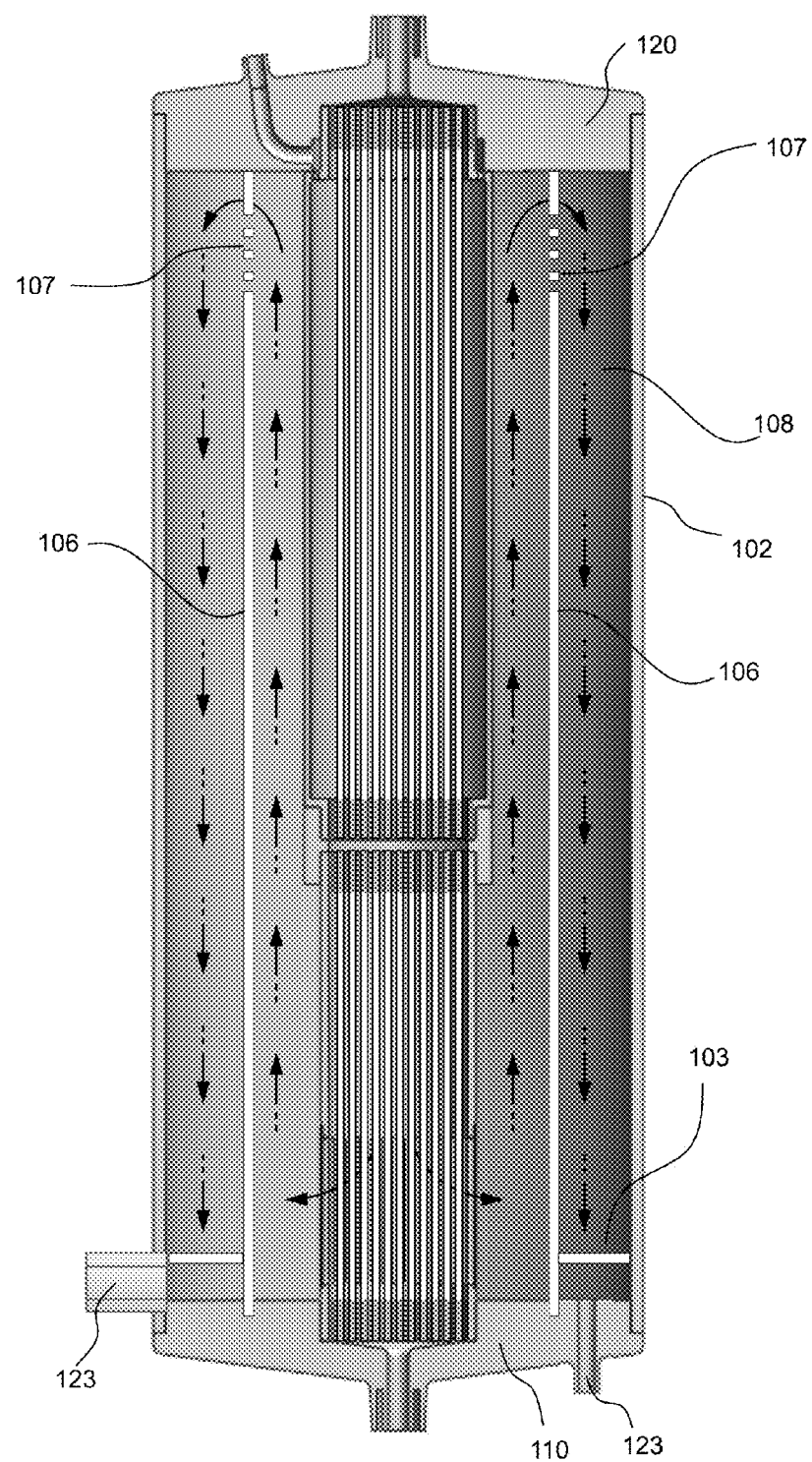
FIG. 10 is a cross-sectional view illustrating a blood purifying filter including an intermediate wall according to a first embodiment of the present invention.

In order to further increase an effective interfacial area between plasma and adsorbent, as shown in FIG. 10, an intermediate wall 106 may be provided in the plasma flow section 108. The intermediate wall 106 may be disposed inside the plasma flow section 108, and fixed on the lower cap 110. Also, the intermediate wall 106 can have an outflow hole 107 at a place close to the upper cap 120. Thus, when the intermediate wall 106 is disposed, the plasma outlet 123 can be desirably disposed at the lower cap 110 or at the wall 102 close to the lower cap 110.

Figure 11:
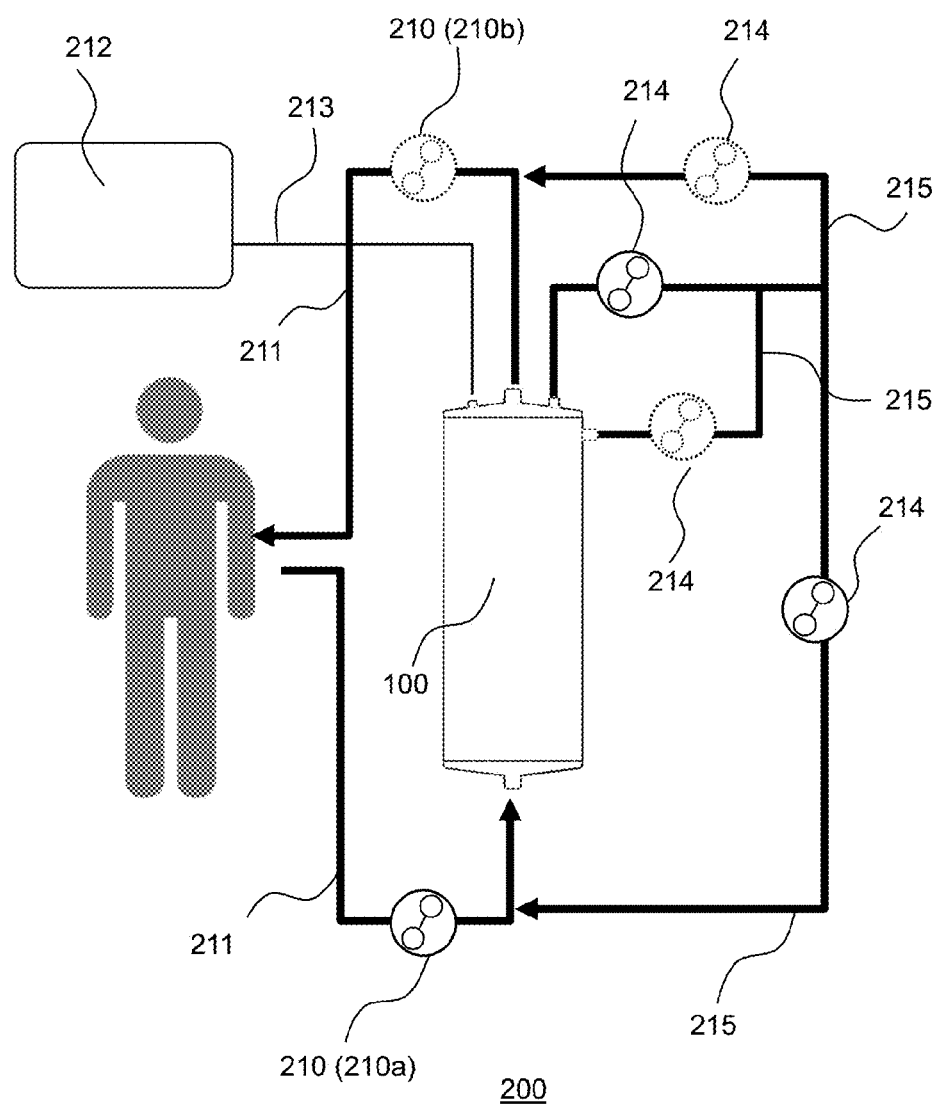
FIG. 11 is a view illustrating a blood purifying apparatus including a blood purifying filter according to a first embodiment of the present invention.
Figure 12:
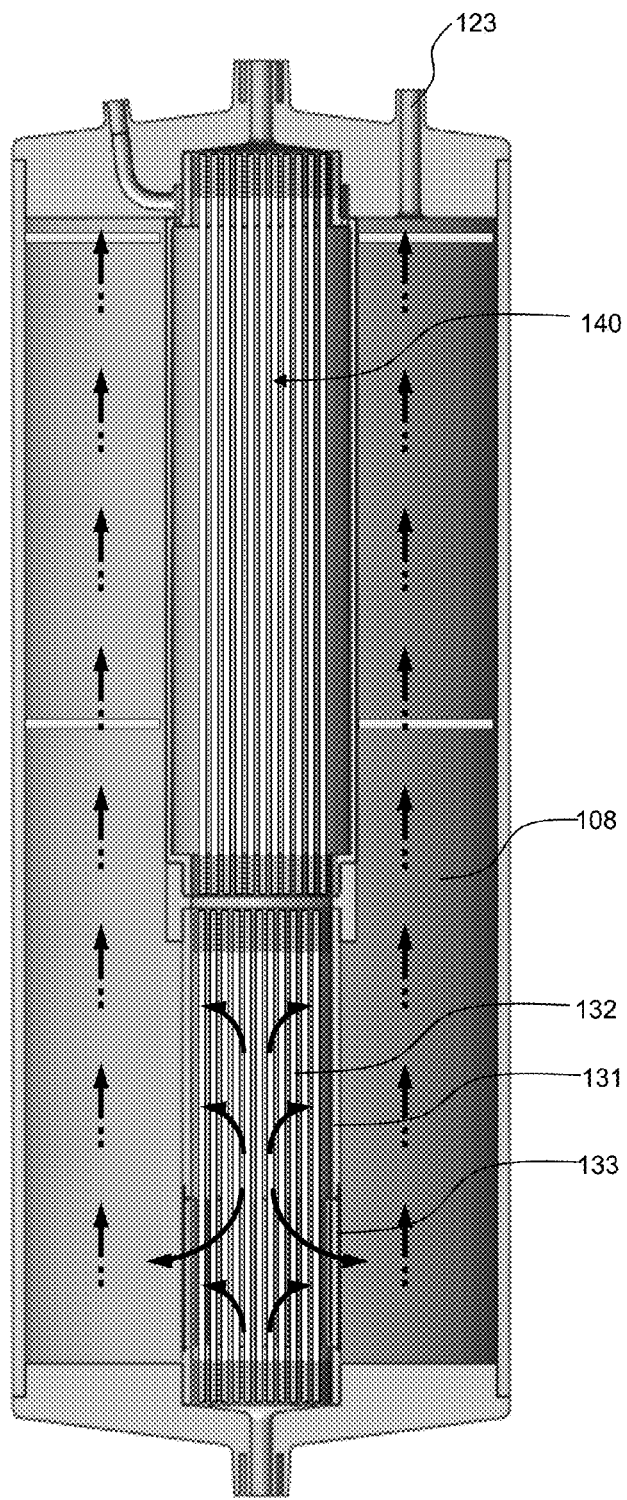
FIG. 12 is a cross-sectional view illustrating a flow of plasma inside a blood purifying filter according to a first embodiment of the present invention.
Figure 13:
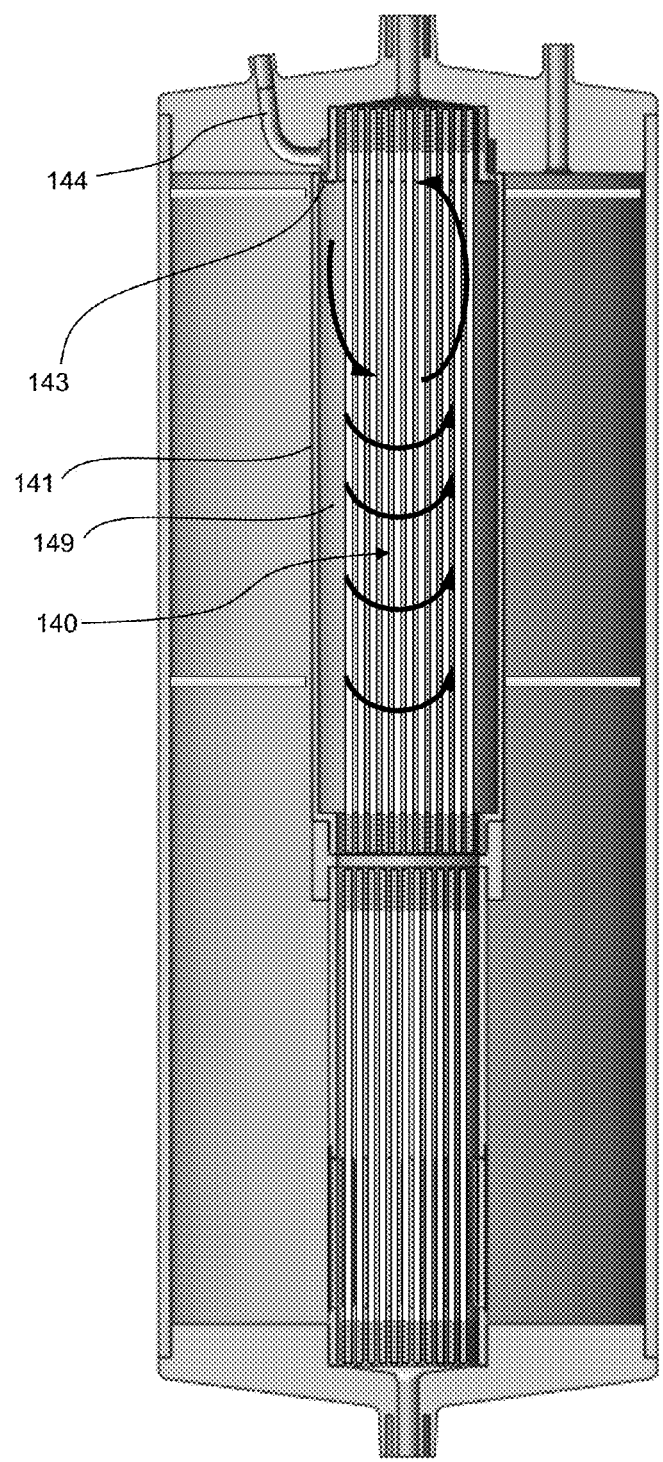
FIG. 13 is a cross-sectional view illustrating a flow of dialysate inside a blood purifying filter according to a first embodiment of the present invention.

Hereinafter, the operation of a blood purifying apparatus 200 including the blood purifying filter 100 according to the first embodiment of the present invention will be described in detail with reference to the accompanying drawings. FIG. 11 is a view illustrating the blood purifying apparatus 200 including a blood purifying filter 100 according to an embodiment of the present invention, and FIG. 12 is a cross-sectional view illustrating the flow of plasma inside the blood purifying filter 100. Also, FIG. 13 is a cross-sectional view illustrating the flow of dialysate inside the blood purifying filter 100.

As shown in FIG. 11, when a blood pump 210 operates and thus blood of a patient flows into the plasma separation filter 130 through the blood port 111 of the lower cap 110, plasma passes through the plasma separation membrane 132 to be separated due to fluid pulling by a plasma pump 214. Remaining blood including blood cells flows into the hemodialysis filter 140 through the connector. Here, toxins and waste products inside blood are removed through hemodialysis, and then blood returns to a patient through the blood port 111 provided in the upper cap 120. The blood purifying filter 100 is connected to a patient through a blood flow tube 211 and the blood pump 210 is disposed on the blood flow tube 211. Similarly, the plasma pump 214 may be disposed on a plasma flow tube 215 connecting the plasma outlet 123 and the blood flow tube 211. As shown in FIG. 11, the blood pump 210 may include a plasma separation blood pump 210a disposed at a front side of the blood purifying filter 100 and a hemodialysis blood pump 210b disposed at a rear side of the blood purifying filter 100 to control the flow rate of blood passing through the plasma separation filter 130 and the hemodialysis filter 140, respectively.

As shown in FIG. 12, separated plasma moves to the plasma flow section 108 through the plasma flow hole 133 provided in the plasma separation filter housing 131. In this plasma flow section 108, toxins and waste products may be removed from plasma through a contact with adsorbent.

Plasma passing through adsorbent returns to the blood flow tube 211 via the plasma pump 214. When there are two plasma outlets 123, the plasma pumps 214 may be connected to the respective plasma outlets 123 to control the flow rate of plasma passing through each of the plasma outlets 123.

Also, as shown in FIG. 13, due to an operation of a dialysate supply device 212, dialysate is supplied to the hemodialysis filter 140 through the dialysate flow passage 144 in the upper cap 120, and discharged out of the hemodialysis filter 140. Thus, when the blood purifying filter 100 has one dialysate flow passage, the supply of dialysate to the hemodialysis filter 140 by the dialysate supply device 212 and the discharge of dialysate that is used may alternately occur. As described above, the dialysate flow passage included in the blood purifying filter 100 according to the first embodiment of the present invention may not only pass through the upper cap 120, but may also vary in shape, location, and number.

The flow of blood may not only return to a patient by sequentially passing through the blood port 111 of the lower cap 110, the plasma separation filter 130, and the hemodialysis filter 140, but may also return to a patient by sequentially passing through the blood port of the upper cap 120, the hemodialysis filter 140, the plasma separation filter 130, and the blood port 111 of the lower cap 110.

In addition to the function of hemodialysis due to the flow of dialysate, the hemodialysis filter 140 can be easily switched into a function of hemofiltration in which excess water and waste products in blood are removed by the fluid pulling due to the dialysate supply device 212 without the supply and discharge of dialysate by the dialysate supply device 212.

Figure 14:
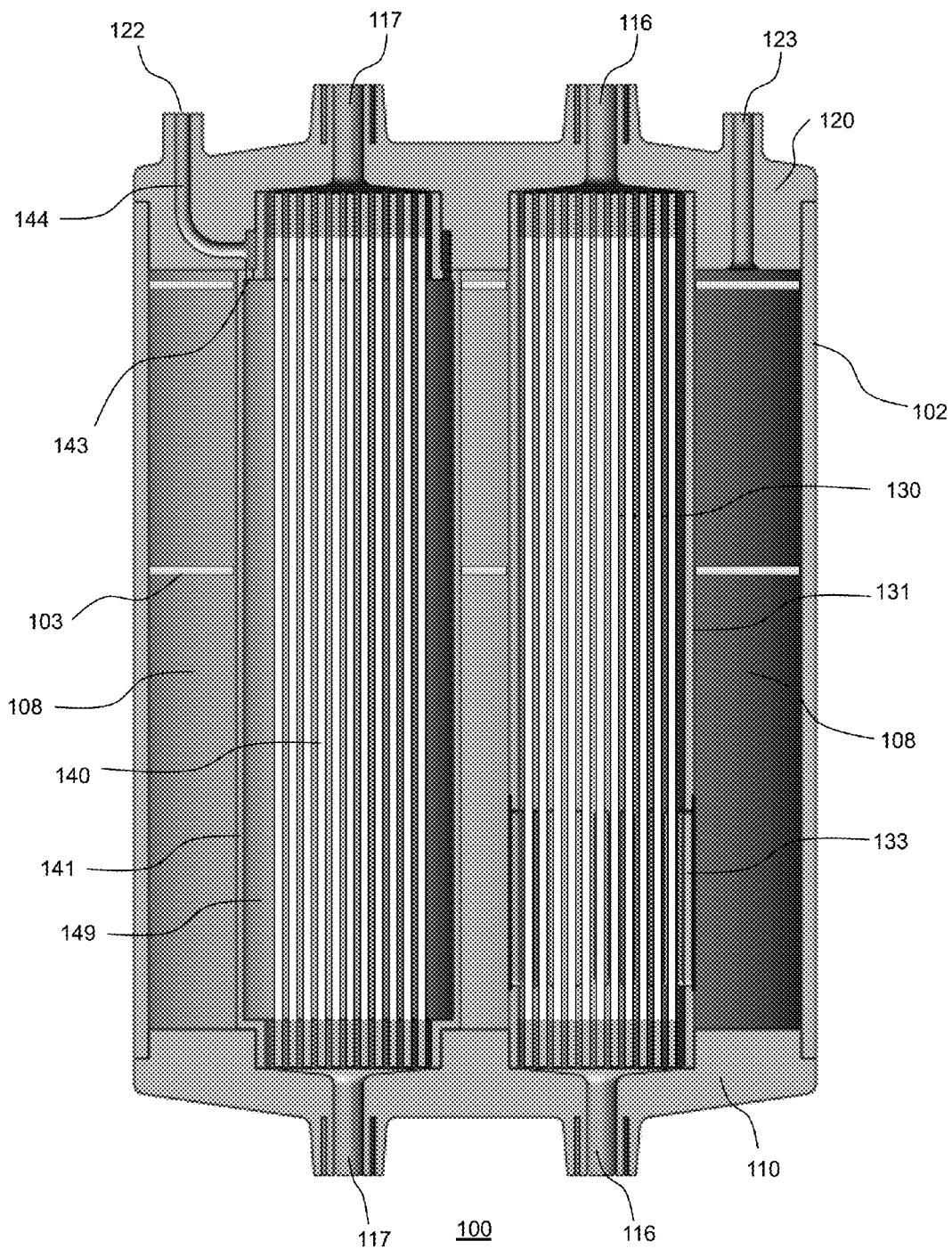
FIG. 14 is a cross-sectional view illustrating an internal configuration of a blood purifying filter according to a second embodiment of the present invention.
Figure 15:
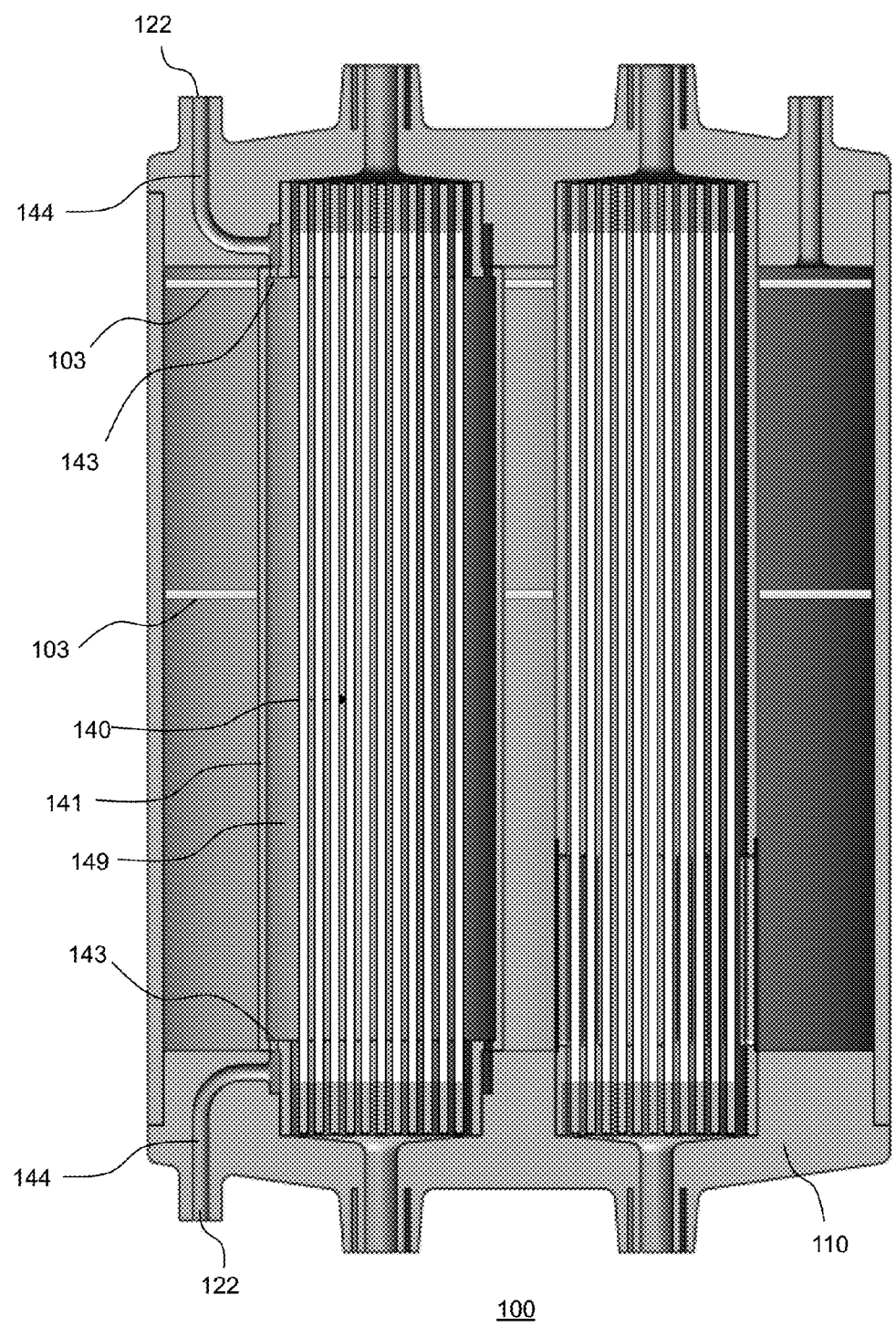
FIG. 15 is a cross-sectional view illustrating a blood purifying filter having two dialysate passages according to a second embodiment of the present invention.

Hereinafter, a blood purifying filter 100 according to a second embodiment of the present invention will be described in detail with reference to the accompanying drawings. FIG. 14 is a cross-sectional view illustrating an internal configuration of a blood purifying filter 100 according to a second embodiment of the present invention, and FIG. 15 is an exploded cross-sectional view of the blood purifying filter 100 having two dialysate flow passages.

As shown in FIG. 14, the blood purifying filter 100 includes a plasma separation filter 130, a hemodialysis filter 140, a housing, and a plasma outlet 123. The plasma separation filter 130 separates plasma from blood that is introduced from one side of the blood purifying filter 100. The hemodialysis filter 140, which is disposed to be parallel to the plasma separation filter 130, removes waste products from blood. The housing provides installation spaces for the plasma separation filter 130 and the hemodialysis filter 140, and defines a plasma flow section 108 outside the plasma separation filter 130 and the hemodialysis filter 140. The plasma outlet 123 allows plasma passing the plasma flow section 108 to be discharged out of the blood purifying filter 100. The housing may include a wall 102 having a cylindrical shape, a lower cap 110 coupled to the plasma separation filter 130 and the hemodialysis filter 140 at a lower side of the wall 102, and an upper cap 120 coupled to the plasma separation filter 130 and the hemodialysis filter 140 at an upper side of the wall 102. The lower cap 110 and the upper cap 120 may include a first blood port 116 and a second blood port 117 that are connected to the plasma separation filter 130 and the hemodialysis filter 140, respectively and may have insertion grooves 112 so as easily to be coupled to the plasma separation filter 130 and the hemodialysis filter 140.

The plasma separation filter 130 is divided into a blood flow region and a plasma flow region by a plasma separation membrane 132 accommodated in the internal space of a plasma separation filter housing 131. The plasma separation filter housing 131 may have a plasma flow hole 133 such that separated plasma can flow into the plasma flow section 108. Both ends of the plasma separation filter 130 are coupled to the lower cap 110 and the upper cap 120, and thus blood passing through the first blood port 116 flows into the blood flow region inside the plasma separation filter 130.

Similarly, the hemodialysis filter 140 is divided into a blood flow region and a dialysate flow region by a hemodialysis membrane 142 accommodated in the internal space of the hemodialysis filter housing 141. Both ends of the hemodialysis filter 140 are coupled to the lower cap 110 and the upper cap 120, and thus blood passing through the second blood port 117 flows into the blood flow region inside the hemodialysis filter 140.

Also, as shown in FIG. 14, a dialysate flow port 122 and dialysate flow holes 143 provided in the upper cap 120 and in the hemodialysis filter housing 141, respectively, may form a dialysate flow passage 144 when the hemodialysis filter 140 is coupled to the upper cap 120. Here, the dialysate flow passage 144 is not limited to the shape and location described in the drawings, and may be modified into other structures that can allow dialysate to flow. For example, the dialysate flow passage 144 passing through the upper cap 120 may be modified so as to pass through the lower cap 110. In addition, as shown in FIG. 15, the dialysate flow passage 144 may be separately formed in the upper cap 120 and the lower cap 110 to separate the inflow and outflow of dialysate.

An adsorbent may be provided in the plasma flow section 108 to remove toxins and waste products from plasma, and the shape, type, and number of adsorbent can be modified according to the purpose of the blood purifying treatment. The plasma flow hole 133 may be provided closely to the lower cap 110 of the plasma separation filter housing 131 and the plasma outlet 123 may be provided in the upper cap 120 or on the wall 102 at a side of the upper cap 120, such that plasma can sufficiently contact the adsorbent inside the plasma flow section 108 and then be discharged.

The adsorbent must not move through the plasma flow hole 133 and the plasma outlet 123. When two or more kinds of adsorbent are used, it is preferable that the two or more kinds of adsorbent do not mix with each other. For this, various methods described above may be used. Finally, in order to further increase the effective interfacial area between plasma and adsorbent, an intermediate wall 106 having an outflow hole 107 disposed closely to the upper cap 120 may be provided. The intermediate wall 106 may be located in the plasma flow section 108, and fixed to the lower cap 110. When the intermediate wall 106 is disposed, the plasma outlet 123 may be desirably disposed in the lower cap 110 or the wall 102 close to the lower cap 110.

Figure 16:
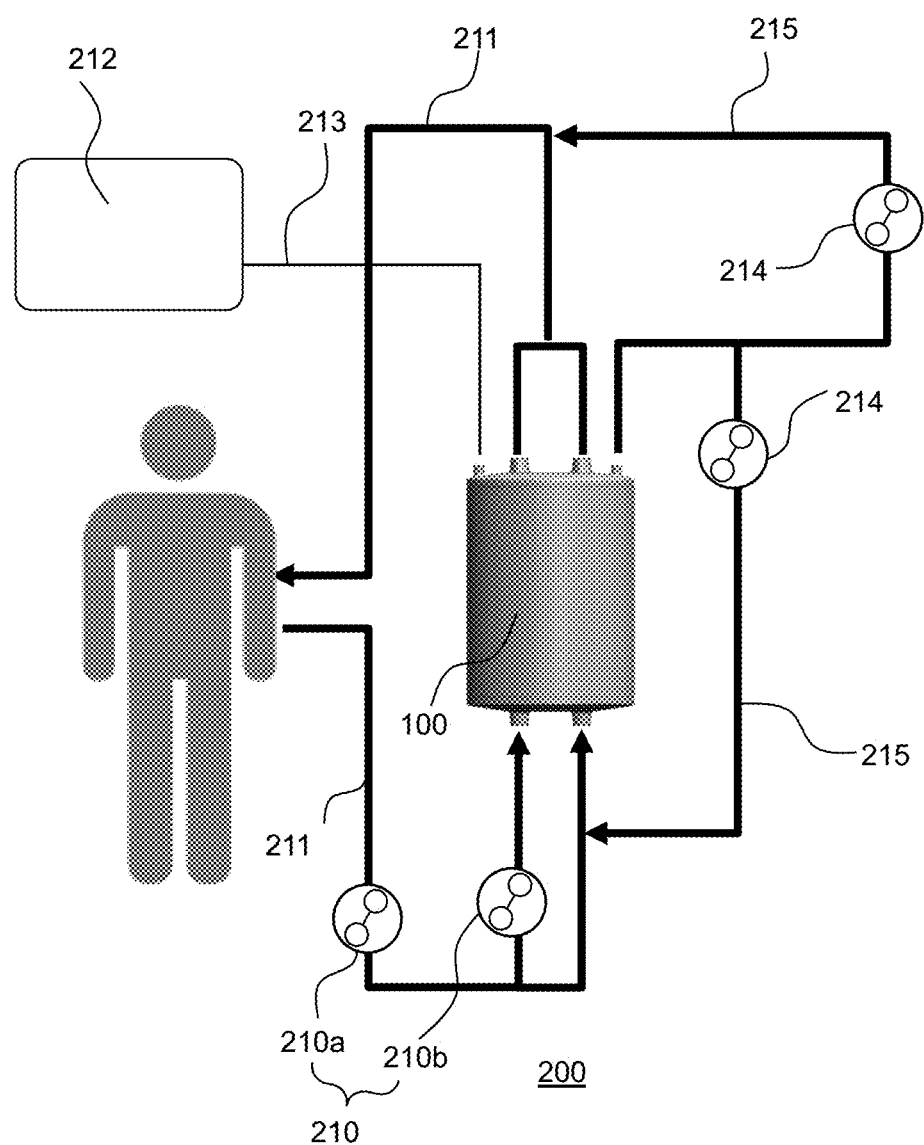
FIG. 16 is a view illustrating a blood purifying apparatus including a blood purifying filter according to a second embodiment of the present invention.

Hereinafter, a blood purifying apparatus 200 including the blood purifying filter 100 according to the second embodiment of the present invention will be described in detail with reference to the accompanying drawings. FIG. 16 is a view illustrating a blood purifying apparatus 200 including a blood purifying filter 100 according to a second embodiment of the present invention.

As shown in FIG. 16, a blood pump 210 operates and thus blood flows into the plasma separation filter 130 and the hemodialysis filter 140 through the first and second blood ports 116 and 117 of the lower cap 110. Due to fluid pulling by a plasma pump 214, plasma passes through the side wall of the plasma separation membrane 132 to be separated, and remaining blood including blood cells returns to a patient through the first blood port 116 of the upper cap 120. Simultaneously, waste products are removed from blood passing through the hemodialysis filter 140, and then blood returns to a patient through the second blood port 117 of the upper cap 120. The blood purifying filter 100 is connected to the body of a patient through a blood flow tube 211 and the blood pump 210 is disposed on the blood pump 210. Similarly, the plasma pump 214 is disposed on a plasma flow tube 215 connecting the plasma outlet 123 and the blood flow tube 211. When there are two plasma outlets 123, the plasma pumps 214 are connected to the respective plasma outlets 123 in order to control the flow rates of plasma passing through each of the plasma outlets 123. As shown in FIG. 16, the blood pump 210 can be separated into a plasma separation blood pump 210*a* and a hemodialysis blood pump 210*b* to control the blood flow rates flowing into the plasma separation filter 130 and the hemodialysis filter 140, respectively.

Separated plasma moves to the plasma flow section 108 through the plasma flow hole 133 provided in the plasma separation filter housing 131. In this plasma flow section 108, toxins and waste products are removed from plasma through a contact between plasma and adsorbent. Plasma passing through adsorbent returns to the blood flow tube 211 via the plasma pump 214.

Also, dialysate is supplied to the hemodialysis filter 140 through the dialysate flow passage 144 of the upper cap 120, or discharged out of the hemodialysis filter 140 by the operation of a dialysate supply device 212. Thus, when the blood purifying filter 100 has one dialysate flow passage, the supply of dialysate to the hemodialysis filter 140 and the discharge of dialysate out of the hemodialysis filter 140 may alternately occur. However, as described above, the dialysate flow passage may not only pass through the upper cap 120, but may also be provided in both of the upper cap 120 and the lower cap 110 and vary in shape, location, and number.

Thus, the blood purifying filters 100 according to the embodiments of the present invention can efficiently purify blood of a patient requiring a blood purification treatment, and enable simplification and miniaturization of the whole blood purifying apparatus, by integrating a plasma separation process for separating plasma from blood, an adsorption process for removing hepatic toxins or protein-bound toxins from the separated plasma, and a hemodialysis process for removing uremic toxins and water-soluble toxins from blood. The blood purifying filters 100 can further provide convenience in installation and reduce a treatment cost by using only one filter.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A blood purifying filter comprising:
   a plasma separation filter separating plasma from blood;
   a hemodialysis filter removing toxins and waste products from blood;
   a housing providing installation space for the plasma separation filter and the hemodialysis filter and defining a flow section outside the plasma separation filter and the hemodialysis filter;
   a fluid outlet provided at one side of the housing, and
   a connector connecting the plasma separation filter and the hemodialysis filter to prevent a blood leakage between the plasma separation filter and the hemodialysis filter, wherein the plasma separation filter comprises a plasma separation filter housing and a membrane accommodated in the plasma separation filter housing and the hemodialysis filter comprises a hemodialysis filter housing and a membrane accommodated in the hemodialysis filter housing.

2. The blood purifying filter of claim 1, wherein the plasma separation filter housing has a first flow hole allowing fluid to flow therethrough.

3. The blood purifying filter of claim 2, wherein the housing comprises:
   a wall having a cylindrical shape;
   a lower cap coupled to the plasma separation filter at a lower side of the wall; and
   an upper cap coupled to the hemodialysis filter at an upper side of the wall.

4. The blood purifying filter of claim 3, wherein the connector has a portion that contacts the plasma separation filter housing and the hemodialysis filter housing.

5. The blood purifying filter of claim 3, wherein the hemodialysis filter housing has a second flow hole at one side thereof, and the upper cap comprises a flow port.

6. The blood purifying filter of claim 5, wherein the second flow hole and the flow port form a flow passage when the upper cap and the hemodialysis filter are coupled to each other.

7. The blood purifying filter of claim 6, comprising an adsorbent disposed in the flow section to purify blood.

8. The blood purifying filter of claim 7, wherein a separation wall is disposed between the adsorbent and the first flow hole or between the adsorbent and the fluid outlet to inhibit passing of the adsorbent.

9. The blood purifying filter of claim 7, further comprising an intermediate wall disposed inside the flow section, fixed on the lower cap, and having an outflow hole at a place close to the upper cap.

10. The blood purifying filter of claim 7, comprising a wall flow passage configured to penetrate the hemodialysis filter housing and the housing wall.

11. The blood purifying filter of claim 7, wherein the first flow hole or the fluid outlet are formed to have a size smaller than the adsorbent.

12. The blood purifying filter of claim 7, wherein the first flow hole or the fluid outlet are covered by a mesh filter with pores having a smaller size than the adsorbent.

13. The blood purifying filter of claim 7, wherein the adsorbent is covered by a mesh filter with pores having a smaller size than the adsorbent.

14. A blood purifying apparatus comprising:
   a blood purifying filter according to claim 7;
   a blood tube connecting between the blood purifying filter and a patient and allowing blood to flow therein;
   a blood pump disposed on the blood tube to transfer blood;
   a fluid tube connecting between a fluid outlet of the blood purifying filter and the blood tube; and
   a fluid pump disposed on the fluid tube to transfer fluid therein.

* * * * *